United States Patent [19]

Omote et al.

[11] Patent Number: 4,892,832
[45] Date of Patent: Jan. 9, 1990

[54] FILTER BAG FOR MICROBIOLOGICAL EXAMINATION

[75] Inventors: Kiyotaka Omote; Yuichi Matsushima; Masami Taki; Harutomo Oshio; Kazuo Shiraishi, all of Tokyo, Japan

[73] Assignee: Toppan Printing Co., Ltd., Japan

[21] Appl. No.: 127,651

[22] Filed: Dec. 2, 1987

[30] Foreign Application Priority Data

Dec. 5, 1986 [JP] Japan .................................. 61-187582
Dec. 5, 1986 [JP] Japan .................................. 61-187583

[51] Int. Cl.$^4$ ............................................ C12M 1/12
[52] U.S. Cl. ..................................... 435/311; 435/287; 383/37; 206/554
[58] Field of Search ................ 435/311, 300, 287, 293, 435/296; 206/554, 569, 494, 570, 538, 0.5; 604/408–410, 333; 73/863.21, 863.23; 383/38–40, 105, 107, 127

[56] References Cited

U.S. PATENT DOCUMENTS

3,520,471 7/1970 Faust ................................. 604/410 X
4,588,554 5/1986 Kaartinen et al. ............... 604/410 X
4,624,365 11/1986 Derdyk .............................. 206/554

FOREIGN PATENT DOCUMENTS

60-33898 8/1985 Japan .
60-33899 8/1985 Japan .

OTHER PUBLICATIONS

Konuma, H. et al., "Improved Stomacher 400 Bag Applicable to the Spiral Plate System for Counting Bacteria", in Applied and Environmental Microbiology, vol. 44, No. 3, Sep. 1982, pp. 765–769.

Primary Examiner—Larry Jones
Attorney, Agent, or Firm—Lerner, David, Littenberg, Krumholz & Mentlik

[57] ABSTRACT

There is here provided a convenient bag used at the time when microorganisms which adhere to a specimen containing a solid material are extracted with a saline solution and are then examined. In this bag, a filter sheet is stuck to plastic film sidewalls so as to extend from the opening inlet to the bottom portion of the sidewalls, so that the bag is divided into two chambers. A specimen and a saline solution are poured into one of the two chambers, and the resulting extract is taken out by a pipet from another chamber.

8 Claims, 2 Drawing Sheets

FILTER BAG FOR MICROBIOLOGICAL EXAMINATION

BACKGROUND OF THE INVENTION

1. Field of the Invention

The present invention relates to a bag which can be used to prepare a sample in examining microorganisms adhering to a piece of bread, a solid material or a specimen containing a solid material.

2. Description of the Prior Art

In the case that a specimen to which microorganisms such as bacteria adhere contains a solid material, a uniform sample solution for examination cannot be obtained directly from such a specimen. In general, therefore, the sample solution has been prepared by first adding a sterilized physiological saline to a specimen, shaking the resulting mixture to wash the specimen, removing the slid material therefrom, and if necessary, further diluting it. As methods for removing the solid material from the mixture of the specimen and the sterilized physiological saline, there are (1) a method of collecting a supernatant liquid after the solid material has precipitated, (2) a method of filtering the mixture with a filter paper, and the like. In addition, for a convenient removal operation, such a bag shown as in FIG. 5 has been also contrived (Applied and Environmental Microbiology, p. 765–769, Sept. 1982). Now, the usage of the bag shown in FIG. 5 will be explained. A mixture is first introduced through an opening inlet of the bag into a large chamber (crude solution chamber) X which is one of two divided chambers in the bag, is then filtered through a filter portion 3 made of a filter paper, is guided into a small chamber (sample solution chamber) Y, and is poured into another container through an outlet of the bag. In FIG. 5, a member E is a heat-sealed partition wall, and a member F is a heat-sealed baffle board for preventing a solid material from flowing out through the opening inlet of the crude solution chamber. This conventional bag is extremely convenient and excellent in which the solid material is separated sanitarily from the crude solution in the bag. However, the prepared sample solution must be transferred to another container which is additionally necessary, and therefore this conventional bag is not always satisfactory.

SUMMARY OF THE INVENTION

The present invention has been made in such a situation, and an object of the present invention is to provide a filter bag in which a solid material can be removed sanitarily from a crude solution and from which a predetermined amount of a sample solution can be taken out by a pipet or the like. Therefore, according to the bag of the present invention, the sample can be added directly to a culture medium by the use of the pipet without requiring any additional container, and the contamination with the solid material can be prevented.

In order to accomplish the above-mentioned object, the present invention provides a filter bag for microbiological examination which is characterized by comprising two sidewalls made from a plastic film, three edges of the sidewalls being sealed, the remaining one edge thereof being opened to form an opening inlet, and a filter sheet extending form the opening inlet to the sealed bottom of the sidewalls, the filter sheet being permeable to a liquid but impermeable to a solid material, the opposite end portions of the filter sheet being stuck to the opposite sidewalls, respectively, so as to divide, into two sections, the interior defined by the sidewalls.

DESCRIPTION OF THE PREFERRED EMBODIMENT

Figures 1A, 1B:
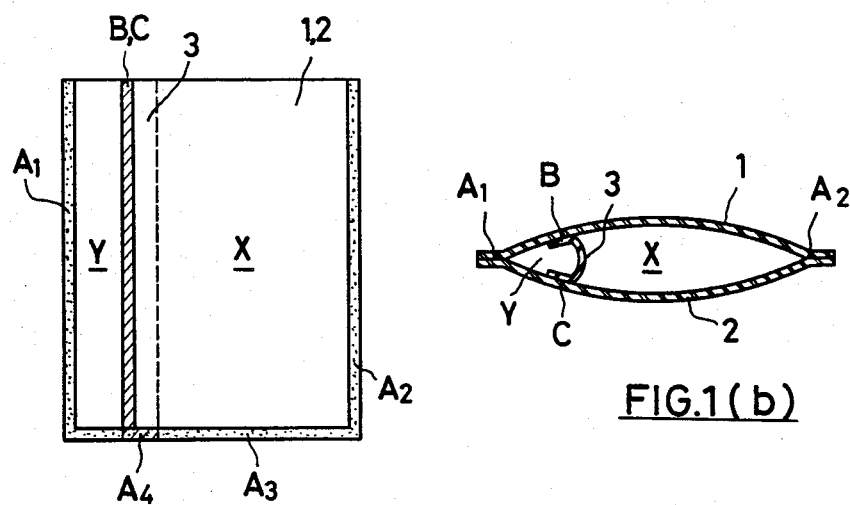
FIGS. 1(a) and 1(b) show an elevation of a bag of the present invention and a cross section illustrating the opened bag.

Referring first to FIGS. 1(a) and 1(b), a bag of the present invention is composed of two sidewalls 1, 2 and a filter sheet 3. In the embodiment in this drawing, the two sidewalls 1, 2 are made from two plastic sheets, but these two sidewalls may be constructed by folding one sheet, needless to say.

The two sidewalls 1, 2 are sealed along three edges A1, A2 and A3 thereof. However, as described hereinafter, the filter sheet 3 is interposed at a position A4 on the bottom sealing edge A3 between the opposite sidewalls 1, 2, and therefore the respective sidewalls 1, 2 are not in contact with each other directly.

As shown in FIG. 1(b), the filter sheet 3 is folded in two and its opposite end portions are stuck to the sidewalls 1, 2. The portion where the filter sheet 3 is stuck to the sidewall 1 is represented by a symbol B and the portion where it is stuck to the sidewall 2 is represented by a symbol C.

At a position A4 where the filter sheet 3 is stuck to the bottom sealing edge A3, the plastic material constituting the opposite sidewalls 1, 2 penetrates through the filter sheet 3, so that the respective portions of the folded filter sheet 3 are joined to each other hermetically at the position A4, that is, so that the opposite sidewalls 1, 2 are joined integrally and hermetically to the filter sheet 3.

Figure 2:
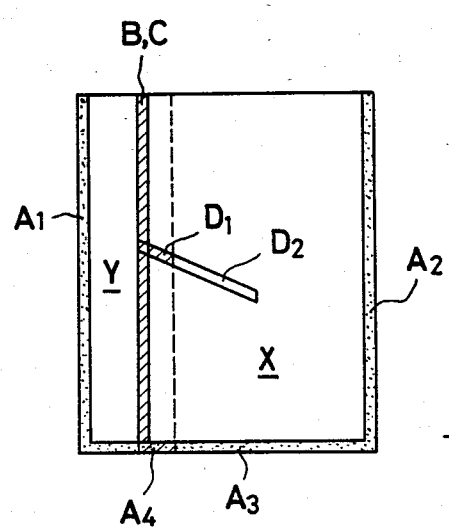
FIG. 2 is an elevation of another embodiment of the present invention.

An embodiment shown in FIG. 2 is identical with the bag in FIG. 1 with the exception that a partition wall D is additionally provided by sealing. This partition wall D can be separated into a portion D1 contacting with the filter sheet 3 and another portion D2 contacting with no filter sheet. At the portion D1, the opposite sidewalls 1, 2 are stuck to the filter sheet 3, but the respective portions of the folded filter sheet 3 are not stuck to each other. At the portion D2, the opposite sidewalls 1, 2 are directly sealed. This partition wall D is not used when taking out a sample solution by a pipet but functions to prevent the sample solution from flowing out from the crude solution chamber X when the sample solution is poured from the sample chamber Y into another container as in the conventional case. Therefore, it is preferred that the partition wall is formed obliquely toward the bottom seal portion A3 in the crude solution chamber X.

Figure 3A:
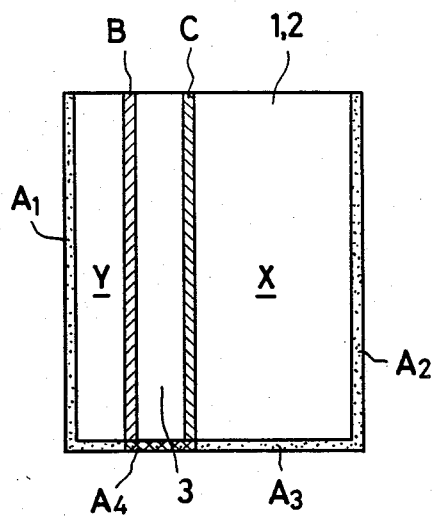
FIGS. 3(a) and 3(b) show an elevation of yet another embodiment of the present invention and a cross section illustrating the opened bag.

In the embodiment in FIGS. 3(a) and(b), a filter sheet 3 is stuck, along the opposite edges thereof, to sidewalls 1, 2. The portion where the filter sheet 3 is stuck on the sidewall 1 is represented by a symbol B and the portion where it is stuck on the sidewall 2 is represented by a symbol C. As understood from the comparison with the embodiment in FIG. 1(b), one end portion of the filter sheet 3 is stuck to the sidewall 1 and the other portion thereof is stuck to the sidewall 2. That is, one surface of the filter sheet 3 is stuck to the sidewall 1 and the other surface thereof is stuck to the sidewall 2. Since FIG. 3(b) shows an opened bag, the filter sheet 3 seems to be in a folded state, but when the bag is closed, the filter sheet 3 is not folded but straight.

Figure 3B:
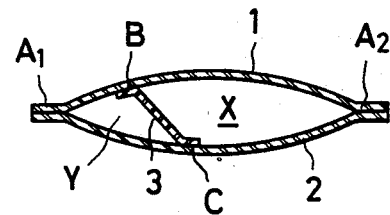
Figure 4:
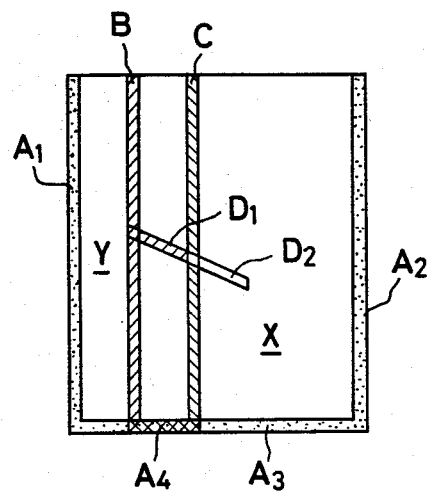
FIG. 4 is an elevation of a fourth embodiment of the present invention.
Figure 5:
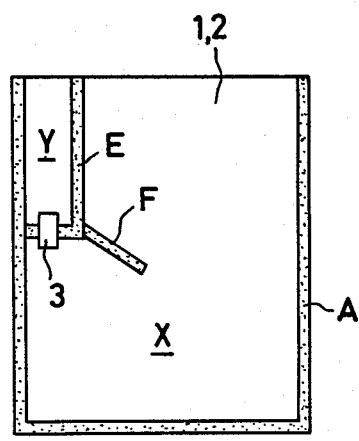
FIG. 5 is an elevation of a conventional bag.

An embodiment shown in FIG. 4 is identical with the bag in FIGS. 3(a) and 3(b) with the exception that a partition wall D is additionally provided. This partition wall D can be separated into a portion D1 contacting with the filter sheet 3 and another portion D2 contacting with no filter sheet 3. At the portion D1, the filter sheet 3 is stuck to the sidewall 1 but is not stuck to the sidewall 2. This bag in FIG. 4 can be used in the same manner as that in FIG. 2.

Examples of the usable raw materials for the sidewalls 1, 2 include plastics such as polyethylenes, polypropylenes, polyesters and the like, and each of these raw materials may be used in the form of a film, a laminate, a film the inside surface of which is coated with a heat-sealing material, or the like. A usable raw material for the filter sheet 3 is a finely porous sheet in which at least either surface has heat-sealing properties and which is permeable to a liquid but impermeable to a solid material, and examples of raw materials for such sheet include synthetic resin nonwoven fabrics, perforated plastic sheets, and the like.

The bags of the present invention can be piled, for example, every 10 bags, put in another large bag, sterilized with a radiation such as gamma rays, and then forwarded. When used, the bag of the present invention is opened. This operation can be easily carried out by sliding the opposite sidewalls 1, 2 on each other at the filter sheet 3 where the sidewalls 1, 2 do not adhere to each other. Then, a specimen such as a piece of bread or the like and a sterilized physiological saline are placed in the crude solution chamber X of the bag. In this case, the total volume of these materials should be limited to one third of the depth of the bag, since when they are too much, the bag is difficult to handle. Afterward, the opening inlet of the bag is clamped hermetically, and the bag is shaken to homogenize the contents therein sufficiently. The thus prepared sample solution is taken out by the use of a pipet or the like.

TEST EXAMPLE 1

A strip-like nonwoven fabric Heat Pack (the Japan Paper Industry Co., Ltd., 18 g/m$^2$) having heat-sealing properties on its one side and Compo Pack (Asahi Chemical Industry Co., Ltd., 20 g/m$^2$) were thermally stuck to the inside surface of a cylindrical film consisting of a polyester (12 μm) and a polyethylene (60 μm), in order to form a partition wall.

Next, the bottom portion of the cylindrical film was pressed at a high temperature to melt the polyethylene sufficiently, so that the latter was allowed to penetrate through the nonwoven fabric material and a strong heatsealing state was obtained, thereby preparing two kinds of bags (which were the same as in FIG. 1).

A large bag consisting of a polyester (12 μm) and a polyethylene (40 μm) was packed with one hundred of the thus prepared examination bags, and was then irradiated with gamma rays of 1.5 Mrod, thereby obtaining the product of the present invention.

Suitable amounts of a potato salad and a sterilized physiological saline were placed in the thus prepared bag of the present invention, and homogenization was then carried out by the use of a stomacher made by A. J. Seward, UAC House, London, England. As a result, a clean sample solution could be prepared in the sample solution chamber and could be taken out by a pipet.

Further, the bag was very easily opened at the portion where the filter sheet was present thereon, since at this portion, the films did not adhere to each other.

TEST EXAMPLE 2

A strip-like nonwoven fabric Melfit (Teijin Limited, 40 g/m$^2$) having heat sealing properties on its one side was thermally stuck to the inside surface of a cylindrical film consisting of a polyester (12 μm) and a polyethylene (60 μm). Next, the bottom portion of the cylindrical film was heated and pressed sufficiently to seal this bottom portion hermetically, thereby preparing bags shown in FIG. 1. Afterward, sterilization was similarly carried out by irradiation with gamma rays.

Subsequently, a potato salad was used as a specimen, and homogenization was then carried out by the use of a stomacher. As a result, a clean sample solution could be prepared in the sample solution chamber and could be taken out by a pipet.

Further, the sidewalls of the bag were very easily opened at the portion where the filter sheet was present thereon, since at this portion, the films did not adhere to each other.

TEST EXAMPLE 3

A strip-like nonwoven fabric BT 0706 W (Teijin Limited, 35 g/m$^2$) having heat sealing properties on its opposite sides was stuck to the inside surface of a cylindrical film consisting of a polyester (12 μm) and a polyethylene (60 μm) so that one surface of the fabric material might be thermally stuck to one sidewall of the bag and the other surface thereof might be thermally stuck to the other sidewall of the bag.

Next, the bottom portion of the cylindrical film was pressed at a high temperature to form a bottom seal, thereby preparing bags (which were the same as in FIG. 3).

A large bag consisting of a polyester (12 μm) and a polyethylene (40 μm) was packed with one hundred of the thus prepared examination bags, and was then irradiated with gamma rays of 1.5 Mrod, thereby obtaining the product of the present invention.

Suitable amounts of a potato salad and a sterilized physiological saline were placed in the thus prepared bag of the present invention, and homogenization was then carried out by the use of a stomacher made by A. J. Seward, UAC House, London, England. As a result, a clean sample solution could be prepared in the sample solution chamber and could be taken out by a pipet.

Further, the bag was very easily opened at the portion where the filter sheet was present thereon, since at this portion, the films did not adhere to each other.

As described above, according to the bag of the present invention, a solid material can be separated sanitarily from a crude solution in the bag, and it is possible to take out a sample solution from the bag by a pipet.

What is claimed is:

1. A filter bag for microbiological examination comprising, opposed sidewalls sealed along the side and bottom edges thereof to form an interior space, and unsealed along the top edges thereof to form an opening inlet, and a filter sheet extending from a top end located at said opening inlet to a bottom end located at the sealed bottom edges of said sidewalls, and attached along one edge thereof to one of said sidewalls and along an opposite edge thereof to another of said sidewalls so as to divide said interior space formed by said sidewalls into two sections, said filter sheet being permeable to a liquid but impermeable to a solid material.

2. The filer bag for microbiological examination as claimed in claim 1 wherein said sidewalls are formed from a plastic film, and said bottom end of said filter sheet is positioned between the bottom edges of said sidewalls, a portion of said plastic film penetrating through said bottom end of said filter sheet in order to hermetically seal said filter sheet to said sidewalls.

3. The filter bag for microbiological examination according to claim 1 wherein a first surface of said filter sheet is used to attach said filter sheet to said opposed sidewalls.

4. The filter bag for microbiological examination according to claim 1 wherein a first surface of said filter sheet is used to attach one edge of said filter sheet to one of said sidewalls, and a second surface of said filter sheet is used to attach the opposite edge of said filter sheet to another of said sidewalls.

5. The filter bag for microbiological examination according to claim 1 further comprising a partition wall projecting obliquely from said filter sheet toward the bottom edges of said sidewalls.

6. The filter bag for microbiological examination according to claim 5 wherein said partition wall is formed by sealing a portion of said sidewalls to one another.

7. A package of filter bags for microbiological examination comprising an outer bag, and a plurality of said filter bags within said outer bag, said package of filter bags having been sterilized, and wherein each of said filter bags comprises opposed sidewalls sealed along the side and bottom edges thereof to form an interior space, and unsealed along the top edges thereof to form an opening inlet, and a filter sheet extending from a top end located at said opening inlet to a bottom end located at the sealed bottom edges of sidewalls, and attached along one edge thereof to one of said sidewalls and along an opposite edge thereof to another of said sidewalls so as to divide said interior space formed by said sidewalls into two sections, said filter sheet being permeable to a liquid but impermeable to a solid material.

8. A package of filter bags for microbiological examination according to claim 7 wherein said sidewalls are formed from a plastic film, and said bottom end of said filter sheet is positioned between the bottom edges of said sidewalls, a portion of said plastic film penetrating through said bottom end of said filter sheet in order to hermetically seal said filter sheet between said sidewalls.

* * * * *